(12) United States Patent
Zachman (10) Patent No.: US 9,936,996 B2
(45) Date of Patent: Apr. 10, 2018

(54) CRYOPROBE HAVING INTERNAL WARMING FLUID CAPABILITIES

(75) Inventor: Andrew K. Zachman, St. Michael, MN (US)

(73) Assignee: Medtronic ATS Medical, Inc., Minneapolis, MN (US)

(*) Notice: Subject to any disclaimer, the term of this patent is extended or adjusted under 35 U.S.C. 154(b) by 1456 days.

(21) Appl. No.: 13/074,731

(22) Filed: Mar. 29, 2011

(65) Prior Publication Data

US 2011/0245821 A1 Oct. 6, 2011

Related U.S. Application Data

(60) Provisional application No. 61/318,974, filed on Mar. 30, 2010.

(51) Int. Cl.
*A61B 18/02* (2006.01)
*A61B 18/00* (2006.01)

(52) U.S. Cl.
CPC .... *A61B 18/02* (2013.01); *A61B 2018/00017* (2013.01); *A61B 2018/00041* (2013.01); *A61B 2018/0212* (2013.01); *A61B 2018/0225* (2013.01); *A61B 2018/0262* (2013.01)

(58) Field of Classification Search
CPC ............ A61B 18/02; A61B 2018/0212; A61B 2018/00041; A61B 2018/00017; A61B 2018/0262; A61B 2018/0225
USPC .................................................... 606/20–26
See application file for complete search history.

(56) References Cited

U.S. PATENT DOCUMENTS

| 3,536,075 | A | 10/1970 | Thomas et al. |
| 4,063,560 | A | 12/1977 | Thomas et al. |
| 6,074,412 | A | * 6/2000 | Mikus et al. ................. 607/105 |
| 6,241,722 | B1 | 6/2001 | Dobak et al. |
| 6,270,493 | B1 | * 8/2001 | Lalonde et al. ................ 606/23 |
| 6,875,209 | B2 | * 4/2005 | Zvuloni et al. ................. 606/21 |
| 7,044,946 | B2 | * 5/2006 | Nahon et al. ................... 606/23 |
| 2001/0037081 | A1 | * 11/2001 | Heiner ........................... 604/23 |
| 2002/0062122 | A1 | * 5/2002 | Lehmann et al. ............. 606/23 |
| 2002/0120267 | A1 | * 8/2002 | Phan ............................... 606/51 |
| 2004/0267248 | A1 | * 12/2004 | Duong et al. ................... 606/21 |
| 2009/0138000 | A1 | * 5/2009 | Vancelette et al. ............. 606/21 |

FOREIGN PATENT DOCUMENTS

| GB | 2093964 A | 9/1982 |
| GB | 2093964 A1 | 9/1982 |
| WO | 9804221 A1 | 2/1998 |
| WO | 2009094640 A1 | 7/2009 |

* cited by examiner

*Primary Examiner* — Joseph Stoklosa
*Assistant Examiner* — Eunhwa Kim
(74) *Attorney, Agent, or Firm* — Christopher & Weisberg P.A.

(57) ABSTRACT

A medical device including elongate probe defining proximal and distal ends and a thermally-transmissive region at its distal end, the elongate probe including a first fluid supply line in fluid communication with the thermally-transmissive region. A second fluid supply line is provided in fluid communication with the thermally-transmissive region, the second fluid supply line being connected to the elongate probe separately from the first fluid supply line. An exhaust line in fluid communication with the first and second fluid supply lines.

17 Claims, 7 Drawing Sheets

CRYOPROBE HAVING INTERNAL WARMING FLUID CAPABILITIES

CROSS-REFERENCE TO RELATED APPLICATION

This application is related to and claims priority to U.S. Provisional Application No. 61/318,974 filed Mar. 30, 2010, the entirety of which is incorporated herein by reference.

STATEMENT REGARDING FEDERALLY SPONSORED RESEARCH OR DEVELOPMENT n/a

FIELD OF THE INVENTION

The present invention relates to a catheters, and more particularly to a cryosurgical catheter system and method for tissue ablation and warming of a thermally-transmissive region of the catheter.

BACKGROUND OF THE INVENTION

It is well documented that atrial fibrillation (AF), either alone or as a consequence of other cardiac disease, continues to persist as the most common type of cardiac arrhythmia. In the United States, AF currently affects an estimated two million people, with approximately 160,000 new cases being diagnosed each year. The cost of treatment for AF alone is estimated to be in excess of $400 million worldwide each year Although pharmacological treatment is available for AF, the treatment is far from perfect. For example, certain antiarrhythmic drugs, like quinidine and procainamide, can reduce both the incidence and the duration of AF episodes. Yet, these drugs often fail to maintain sinus rhythm in the patient. Cardioactive drugs, like digitalis, Beta blockers, and calcium channel blockers, can also be given to control AF by restoring the heart's natural rhythm and limiting the natural clotting mechanism of the blood. However, antiarrhythmic drug therapy often becomes less effective over time. In addition, antiarrhythmic drug can have severe side effects, including pulmonary fibrosis and impaired liver function.

Another therapy for AF is surgery. In a technique known as the "Maze" procedure, a surgeon makes several incisions through the wall of the atrium with a scalpel and then sews the cuts back together, creating a scar pattern. The scars isolate and contain the chaotic electrical impulses to control and channel the electrical signals. The Maze procedure is expensive, complicated to perform, and associated with long hospital stays and high morbidity.

An alternative to open heart or open chest surgery is a minimally invasive "cryo-maze" procedure in which a cryosurgical catheter is used to form ablative scars in various locations in the atrial tissue. This method creates the same scar pattern more easily than the "Maze" procedure and leaves the connective tissue intact as opposed to cutting it. The cryosurgical catheter includes a handle, a highly flexible shaft, and a flexible thermally-transmissive region, where the handle, the shaft, and the thermally-transmissive region define a fluid pathway which is in fluid communication with the fluid supply. The cryogenic fluid can be in a liquid or a gas state. An extremely low temperature can be achieved within the catheter, and more particularly on the surface of the catheter by cooling the fluid to a predetermined temperature prior to its introduction into the catheter or, alternatively, by using Joule-Thomson expansion of the cooling gas in the thermally-transmissive region. The catheter is then introduced into the patient and the thermally-transmissive region contacts the area of the heart where the surgeon desires to form scar tissue.

However, a significant problem with cryosurgical catheters is that when extreme cold is applied to the heart tissue the thermally-transmissive region adheres to the tissue and the surgeon must apply warm saline other fluid to release it. This necessarily results in an extended procedure time because first, warm fluid needs to be applied to the surgical site and then excess fluid must be manually suctioned from the patient. In addition, the extended procedure time presents possible risk to the patient as the patient prolongs the period of time spent under anesthesia.

Thus, it would be desirable to provide a catheter having an internal source of warming fluid to enable the surgeon to quickly and easily thaw the thermally-transmissive region of the catheter.

SUMMARY OF THE INVENTION

The present invention advantageously provides a method and system for warming the thermally-transmissive region of a medical device. The system comprises a medical device including elongate probe defining proximal and distal ends and a thermally-transmissive region at its distal end, the elongate probe including a first fluid supply line in fluid communication with the thermally-transmissive region; a second fluid supply line in fluid communication with the thermally-transmissive region, the second fluid supply line being connected to the elongate probe separately from the first fluid supply line; and an exhaust line in fluid communication with the first and second fluid supply lines.

In another embodiment, the system includes a catheter having a thermally-conductive region at its distal end, the catheter including a fluid injection tube in fluid communication with the thermally-conductive region; at least one laser light emitting element disposed within the thermally-conductive region; a first controller in fluid communication with the fluid injection tube operable to regulate the flow of cryogenic fluid into the thermally-conductive region; and a second controller in optical communication with the laser light emitting element, the second controller including a laser beam generation element.

In yet another embodiment, the method includes positioning a thermally-transmissive region of a medical device proximate a target tissue region; circulating cryogenic fluid toward the thermally-transmissive region through a first fluid supply line; freezing the target tissue region; and warming the thermally-transmissive region sequentially after cooling the target tissue region by circulating a warming fluid within the thermally-transmissive region.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
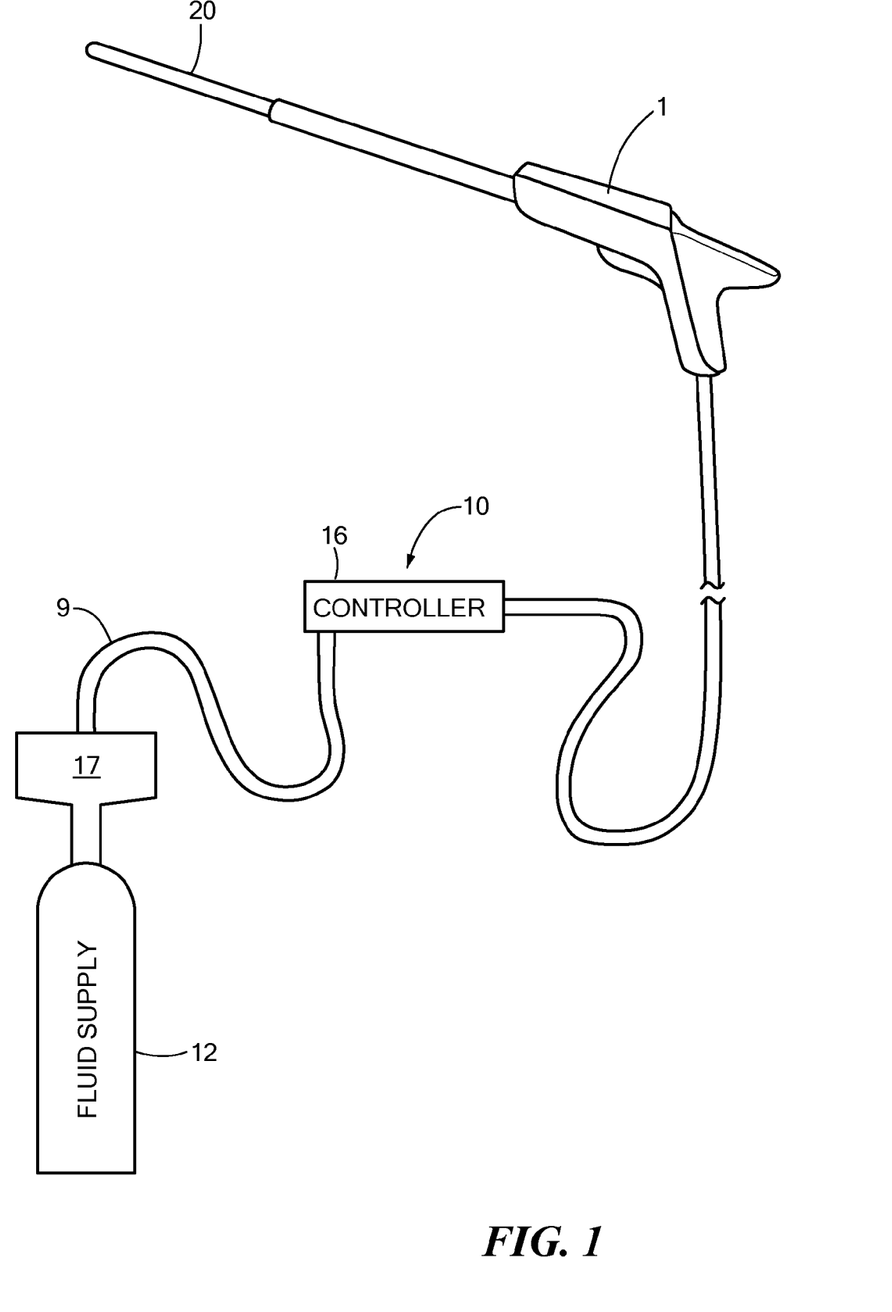
FIG. 1 illustrates an ablation control system used with an ablation catheter in accordance with the present invention.
Figure 2:
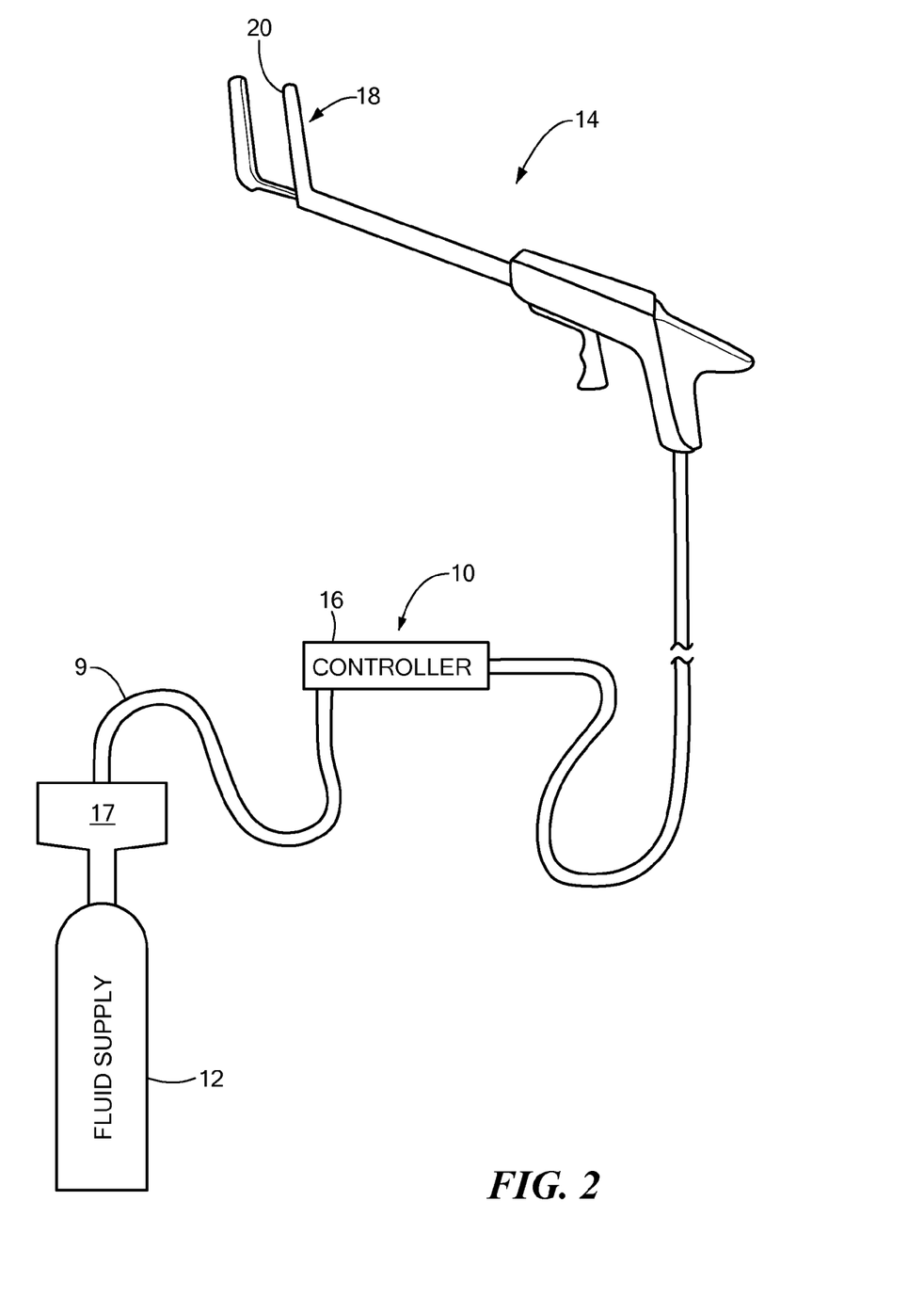
FIG. 2 illustrates the ablation control system of FIG. 1, with the ablation catheter in a clamp in accordance with the present invention.

FIG. 1 is an illustration of a typical cryosurgical system 10. The system includes a supply of cryogenic or cooling fluid 12 in communication with the proximal end of a flexible cryoprobe or catheter 20 including operator handle 1. Alternatively, as seen in FIG. 2, cryoprobe 20 is operably and removably receivable within at least one of two blades or jaws 18 of a cryoclamp 14. For example, the catheter 20 may be insertable within a groove (not shown) defined by at least one of the jaws 18 and/or insertable within a portion of handle 1.

Continuing to refer to FIGS. 1 and 2, a regulator 17 may be interposed or in-line between the cryogenic fluid supply 12 and a controller 16. Controller 16 may be in-line between the regulator 17 and the ablation catheter 14 for controlling and regulating the flow of cryogenic fluid into the catheter in response to a controller command. Controller 16 commands may include programmed instructions, sensor signals, and manual user input. For example, the controller 16 may be programmed or configured to increase and decrease the pressure of a fluid by predetermined pressure increments over predetermined time intervals. In another example, the controller 16 may be responsive to input from a foot pedal to permit flow of the cryogenic fluid into the catheter 20. Alternatively, the controller 16 and regulator 17 may be a single integral component.

One or more temperature sensors (not shown) in electrical communication with the controller 16 may also be provided to regulate or terminate the flow of cryogenic fluid into the catheter 20 when a predetermined temperature at a selected point or points on or within the catheter is/are obtained. For example, a temperature sensor can be placed at a point proximate the distal end of the catheter and other temperature sensors can be placed at spaced intervals between the distal end of the catheter and another point that is between the distal end and the proximal end.

The cryogenic fluid may be circulated in a liquid or a gaseous state. An extremely low temperature may be achieved, for example −80° C. or colder, within the catheter, and more particularly on the surface of the catheter by cooling the fluid to a predetermined temperature prior to its introduction into the catheter, by allowing a liquid state cryogenic fluid to boil or vaporize, or by allowing a gas state cryogenic fluid to expand. Exemplary cryogenic liquids include chlorodifluoromethane, polydimethylsiloxane, ethyl alcohol, HFC's such as AZ-20 (a 50-50 mixture of difluoromethane & pentafluoroethane sold by Allied Signal), and CFC's such as DuPont's FREON. Exemplary cryogenic gasses include nitrous oxide, argon, and carbon dioxide.

Figure 3:
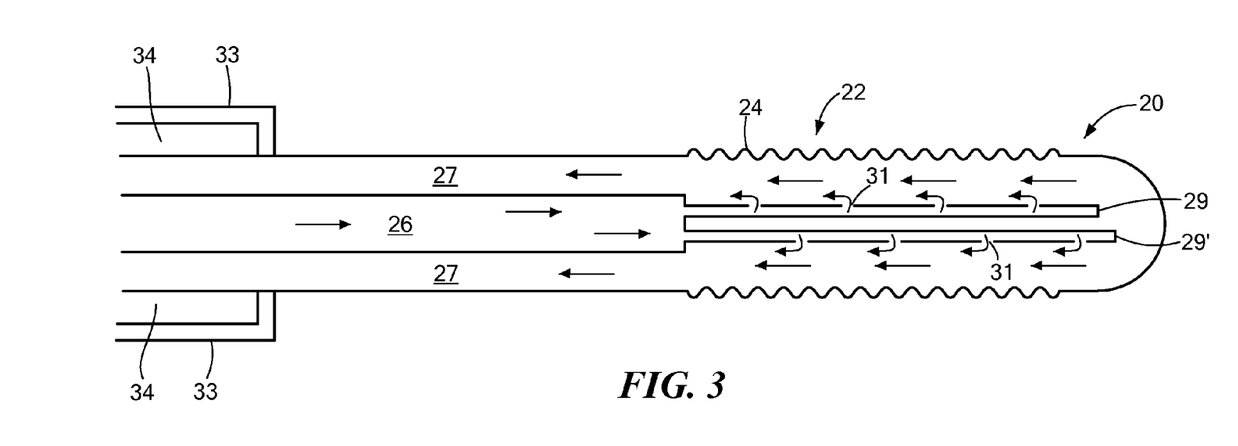
FIG. 3 is a cross-sectional view of an ablation catheter.

Referring to FIG. 3, an ablation catheter 20 generally includes a flexible member 22 having a thermally-transmissive region 24 and a first or cooling fluid supply line 26 that defines a fluid path for cooling fluid to circulate through the flexible member 22 to the thermally-transmissive region 24. The catheter 20 may further define a fluid exhaust path 27 that exhausts the cooling or cryogenic fluid from the thermally-transmissive region 24 to a point external to the catheter at, for example, the proximal end (not shown) thereof. The fluid exhaust path 27 may be concentric with or co-axially aligned with the cooling fluid supply line 26. Exemplary fluid paths can be one or more channels defined by the flexible member 24, and/or by one or more additional flexible members that are internal to the first flexible member 24. Also, even though many materials and structures can be thermally conductive or thermally transmissive if chilled to a very low temperature and/or cold soaked, as used herein, a "thermally-transmissive region" is intended to broadly encompass any structure or region of the catheter 14 that readily conducts heat. For example, a metal structure exposed (directly or indirectly) to the cryogenic fluid path is considered a thermally-transmissive region even if an adjacent polymeric or latex portion also permits heat transfer, but to a much lesser extent than the metal. Thus, the thermally-transmissive region 24 may be viewed as a relative term to compare the heat transfer characteristics of different regions or structures, regardless of the material.

The thermally-transmissive region 24 of the catheter 14 may be deformable and/or semi-rigid such that it retains its shape until a force is applied to it that changes it to a second shape. An exemplary deformation is from a linear configuration to an arcuate configuration and is accomplished using mechanical means known to those skilled in the art such as for example a bellows configuration. Other examples include a wall portion of the flexible member 22 can include a metal braid to make the catheter torqueable for overall catheter steering and placement. Additionally, a cord, wire or cable can be incorporated with, or inserted into, the catheter for deformation of the thermally transmissive region 24.

As illustrated in FIG. 3, the thermally-transmissive region 24 may have a generally bellows-shaped or corrugated configuration. In another example, the thermally-transmissive region 24 may include, for example, a single, continuous, and uninterrupted surface or structure. In yet another example, the thermally-transmissive region 24 may include multiple, discrete, thermally-transmissive structures that collectively define a thermally-transmissive region that is elongate or linear. Depending on the ability of the cryogenic system, or portions thereof, to handle given thermal loads, the ablation of a tissue region may be performed in a single or multiple cycle process with or without having to relocate the ablation catheter 20 one or more times across tissue.

As also illustrated in FIG. 3 cooling fluid supply line 26 may branch at the proximal end of the thermally-transmissive region 24 into two cooling fluid supplies 29, 29. Cooling fluid inlets 29, 29' may be in co-axial relationship with fluid exhaust path 27 defined by outer surface of catheter 20. Alternatively, cooling fluid supply line 26 may run as a single inlet (not shown) into thermally-transmissive region 24. Ablation catheter 20 may further be circumferentially surrounded at the proximal end by a jacket 33 having a lumen 34 therewithin that receives cooling fluid supply line 26 and that is operably connected with controller 16. Fluid supply lines 29, 29' each include a plurality of Joule-Thomson orifices 31 along the longitudinal length thereof. Fluid supply lines 29, 29' may be alternatively be capped at the distal end such that cooling fluid is sprayed through the orifices 31. As the cooling gas expands through Joule-Thomson orifices 31 it is channeled into fluid exhaust path 27 and releases to atmosphere at, for example, the proximal end of jacket 33.

Figure 4:
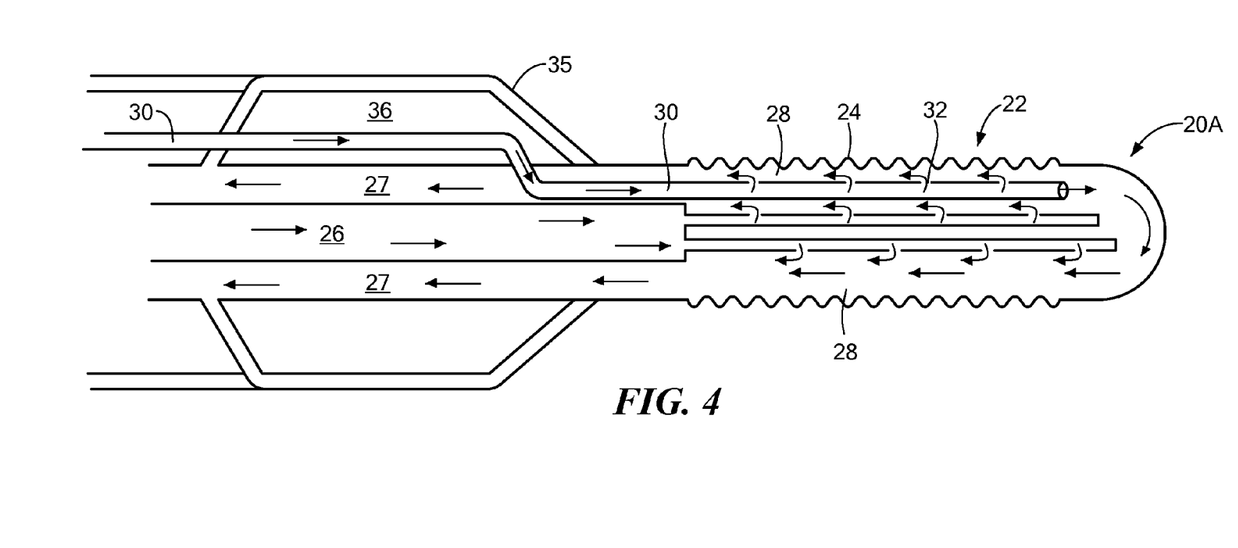
FIG. 4 is a cross-sectional view of an embodiment of an ablation catheter in accordance with the present invention depicting a warming conduit.

FIG. 4 illustrates an exemplary embodiment of an ablation catheter 20 in accordance with the invention. In particular, ablation catheter 20A is similar to ablation catheter 20 previously described above in reference to FIG. 3. However, ablation catheter 20A may include a second or warming fluid supply line 30 adapted to circulate warming fluids such as room temperature air, warmed argon, warmed helium, or an insulating fluid. Warming fluid inlet line 30 may include a plurality of exhaust ports 32, which may be laser drilled openings along the length thereof, which releases a warming element, such as a gas or liquid into the thermally-transmissive region 24 where it exchanges heat with its surroundings. In particular, the warming fluid inlet line 30 may wrap around the fluid supply line 26 or may be linearly disposed within the catheter to provide for a particular spray distribution of warming fluid. The warming fluid may be exhausted though exhaust fluid pathway 27 and to the proximal end of jacket 33 and then to atmosphere.

The warming fluid supply line 30, fluid supply line 26, and fluid exhaust 27 may be each connected to the proximal end of the catheter or probe 20 at separate and distinct locations, such that each fluid line may be fluidicly and thermally isolated from each other. In particular, the warming fluid supply line 30 may be spaced a distance from the fluid supply line 26 and the fluid exhaust 27 such that colder fluid circulating in the fluid supply line 26 and exhaust 27 are thermally isolated from the warming fluid supply line 30 in part to maintain the temperature of the fluid within the warming fluid supply line 30. Further, because the warming fluid supply line 30 and fluid supply line 26 are attached to the medical device 26 separately, they may each be independently and sequentially operable for the flow of fluid into each respective fluid line. For example, the controller 16 may be operable to circulate warming fluid into the warming fluid supply line 30 after cryogenic fluid has been exhausted from the thermally-transmissive region.

Alternatively, the fluid exhaust 27 may surround and be co-axially with the warming fluid supply line 30 to thermally isolate it from the fluid supply line 26. For example, an annular pathway 36 may be created by a connector 35 and be operably connected with jacket 33 and lumen 34. Warming fluid inlet line 30 may be positioned through lumen 34 and annular pathway 36 in parallel relationship to co-axially formed inlet supply line 26 and exhaust pathway 27.

Figure 5:
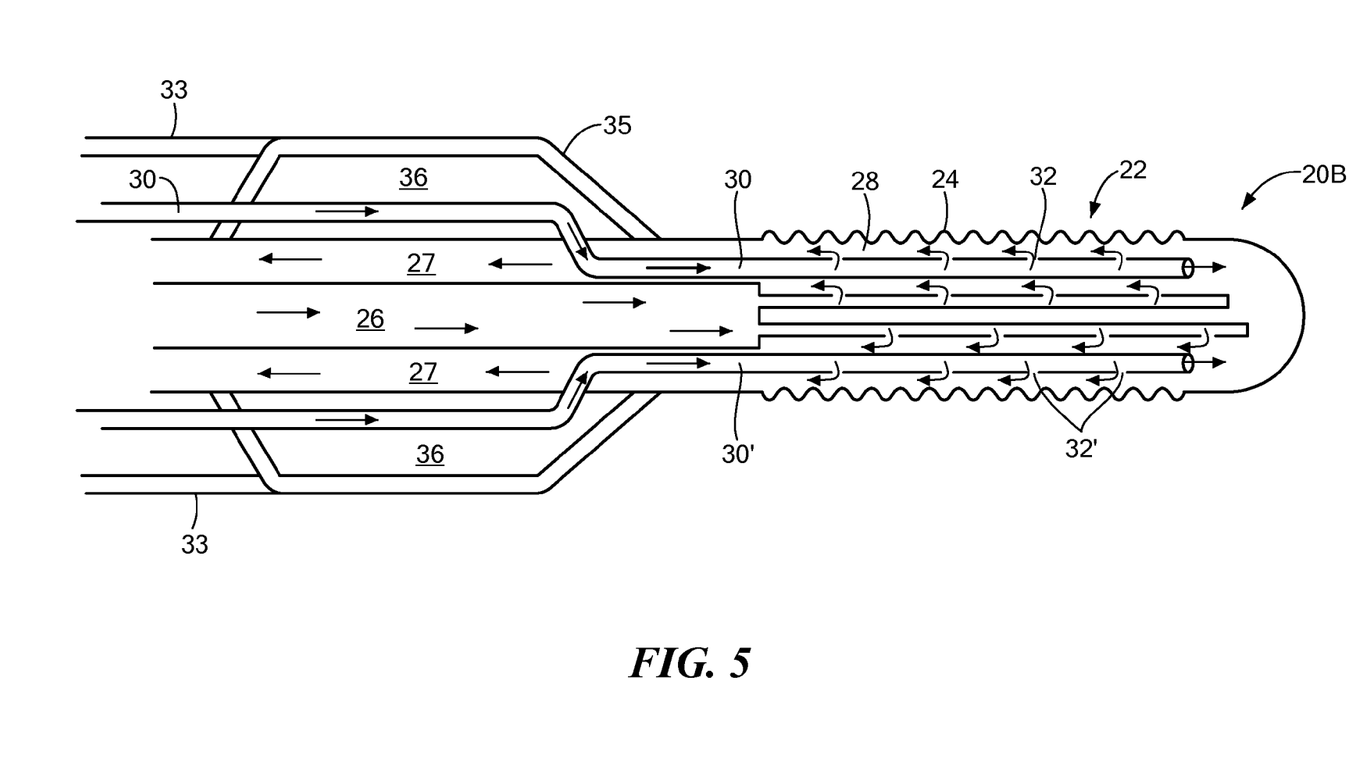
FIG. 5 is a cross-sectional view of an embodiment of an ablation catheter in accordance with the present invention depicting two warming conduits.

FIG. 5 illustrates another example of an ablation catheter 20B. In particular, ablation catheter 20B is similar to ablation catheter 20A previously described above in reference to FIG. 4. However, ablation catheter 20B includes dual warming fluid supply lines 30, 30'. Warming fluid supply lines 30, 30' include a plurality of exhaust ports 32 along the length thereof, which exhausts the warming fluid gas into exhaust fluid pathway 27 and to eventually to atmosphere. Annular pathway 36 is created by connector 35 operably connected with jacket 33 and lumen 34. Warming fluid supply lines 30, 30' are positioned through lumen 34 of jacket 33 and through annular pathway 36 and is aligned in parallel relationship to co-axially formed supply line 26 and exhaust pathway 27.

Figure 6:
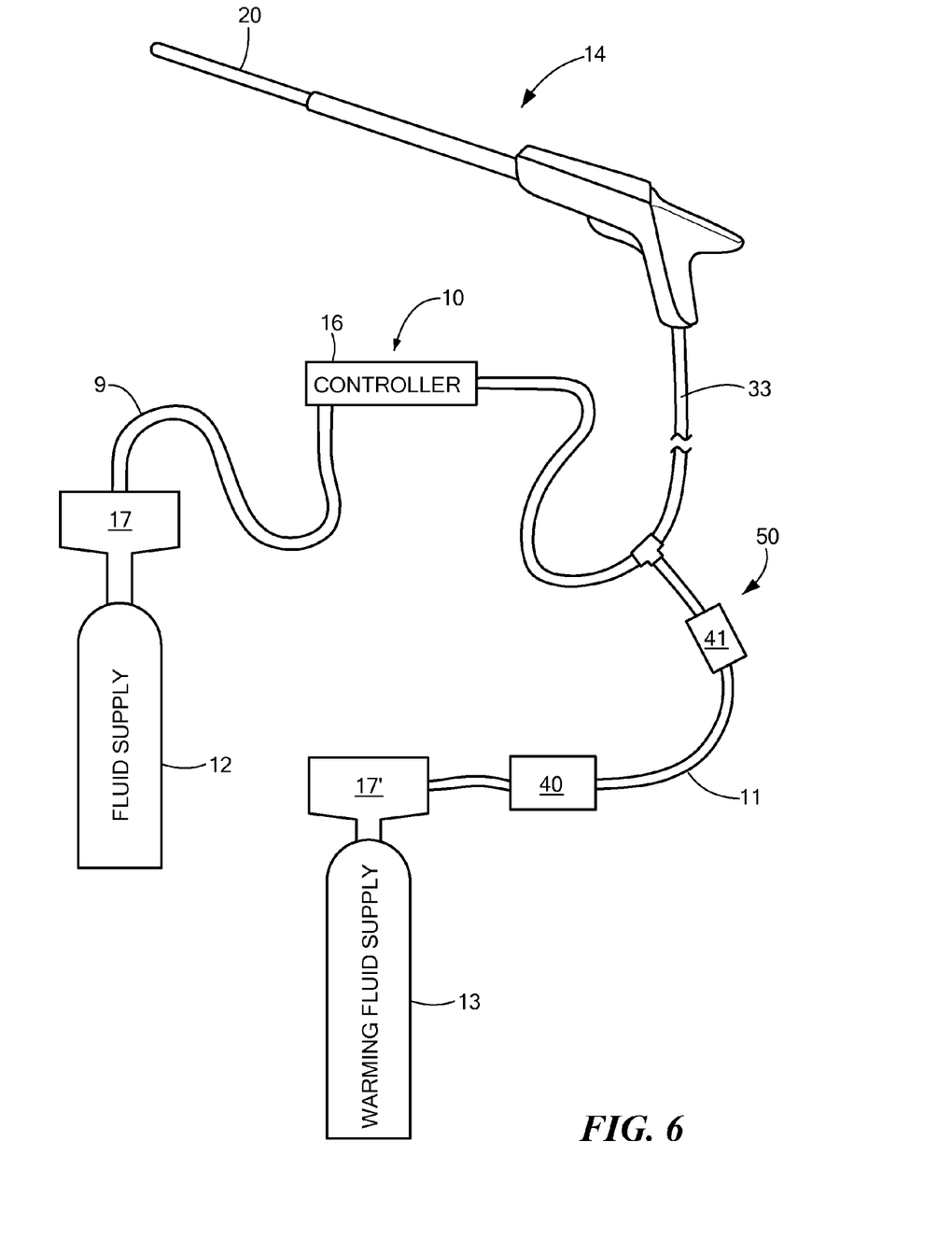
FIG. 6 illustrates an exemplary ablation control system including warming fluid conduit and heater used with the ablation catheter in accordance with the present invention.

FIG. 6 is a schematic illustration of a cryosurgical system 50 in accordance with the invention. The system includes a supply of cryogenic or cooling fluid 12 in communication with a regulator 17 interposed in line. A regulator 17 is interposed or in-line between the cryogenic fluid supply 12 and the supply line 9 that operably connects with controller 16. Regulator 17 regulates the rate and pressure at which the cooling fluid is fed through supply line 9. Jacket 33 which houses the fluid supply line 26 that feeds cryoprobe 20 is connected to the proximal end of flexible cryoprobe 20. Cryoprobe 20 may operably be received within the blades of a cryoclamp 14 (as shown in FIG. 2). The controller 16 is in-line between the fluid supply line 26 and the ablation catheter 20 for controlling and regulating the flow of cryogenic fluid into the catheter in response to controller commands, as discussed above.

A warming fluid line 11 may be provided to circulate the warming fluid from a warming fluid source 13. After the cooling/ablating cycle, warming fluid may be circulated through the controller 16 through a warming fluid supply line 30, which may be in fluid communication with the warming fluid source, toward the thermally-transmissive region 24 where it may be expanded through the plurality of Joule-Thomson exhaust ports 31. As the warming fluid is Joule-Thomson expanded, the thermally-transmissive region 24 warms and may melt an ice ball that has formed on the surface of the thermally transmissive region.

Warming fluid line 11 may further operably connect with second regulator 17'. A second regulator 17' may regulate the flow of warming fluid to warming device 40. Warming device 40 may comprise a heated water bath. If using a heated water bath, warming supply line 11 may comprise copper coil and be coiled within water bath to increase the surface area of the warming fluid that passes therethrough. Warmed warming fluid exits water bath and through the distal area of warming fluid supply line 30. Warming fluid supply line may join the jacket 33 at a proximal end thereof and passes therethrough in parallel relationship to catheter 20. Warming fluid supply line 30 fluidly connects with catheter 20A and 20B as shown in FIGS. 4 and 5. Warming fluid and cooling fluid may comprise argon.

Alternatively, a warming device 40 may be included to heat the warming fluid and further comprise an in-line electric heater with integral heat exchanger therewithin. Warming supply line 11 operably connects with in-line electric heater to warm the warming fluid. Warmed warming fluid exits electric heater and passes through the distal area of warming fluid supply line 30. Warming fluid supply line 30 joins jacket 33 at a proximal end thereof and passes therethrough in a substantially parallel relationship to catheter 20. Warming fluid supply line 30 fluidly connects with catheter 20A and 20B as shown in FIGS. 4 and 5. Warming device 40 and regulator 17' may be housed within warming supply controller 41, which may regulate the flow of fluid into the warming fluid supply line 30. Alternatively, controller 16 may be in fluid communication with both the fluid supply 12 and the warming fluid supply 13 to regulate the flows of both fluids from a single controller.

Figure 7:
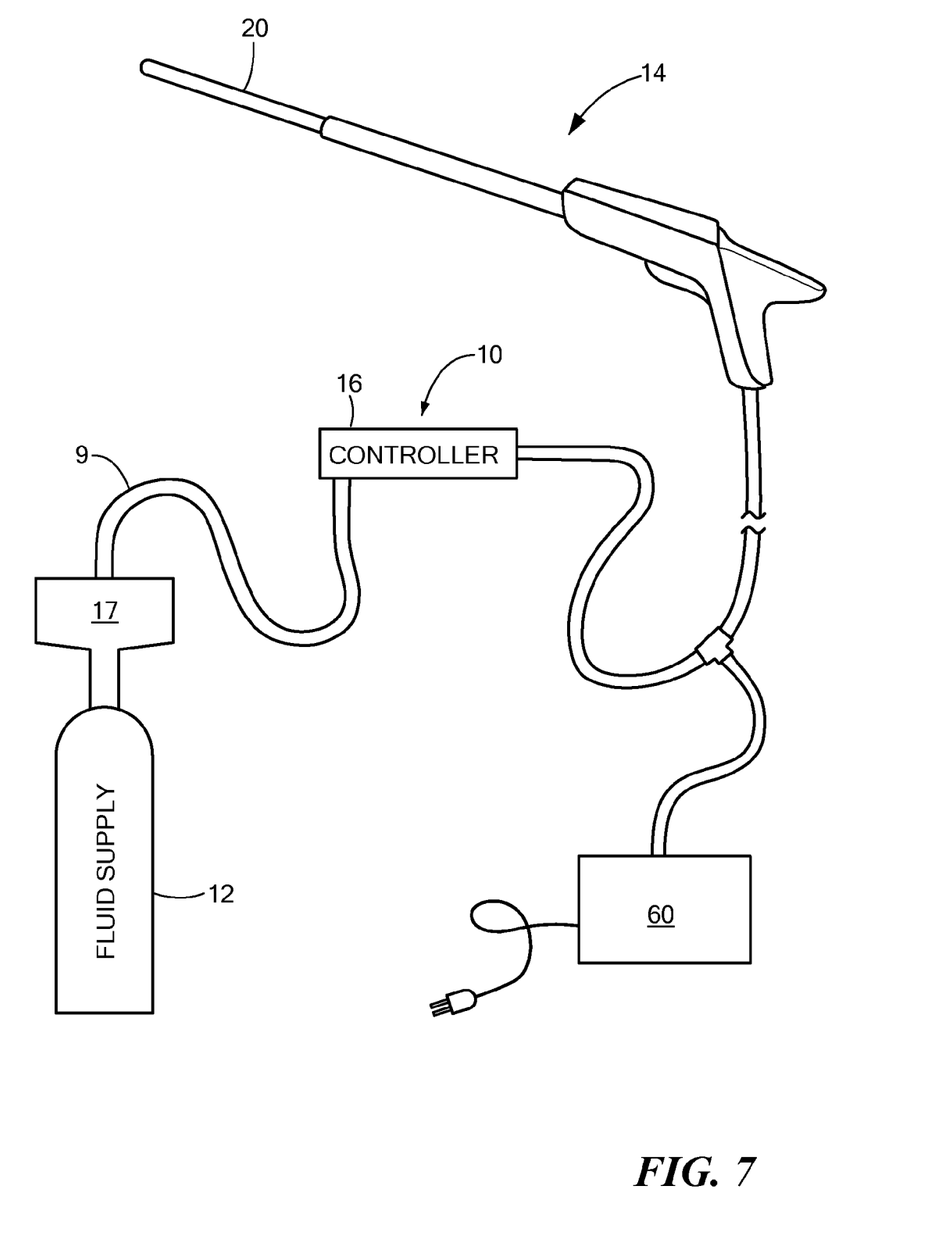
FIG. 7 illustrates an exemplary ablation control system including controller with integrated laser and fiber optic line in accordance with the present invention.
Figure 8:
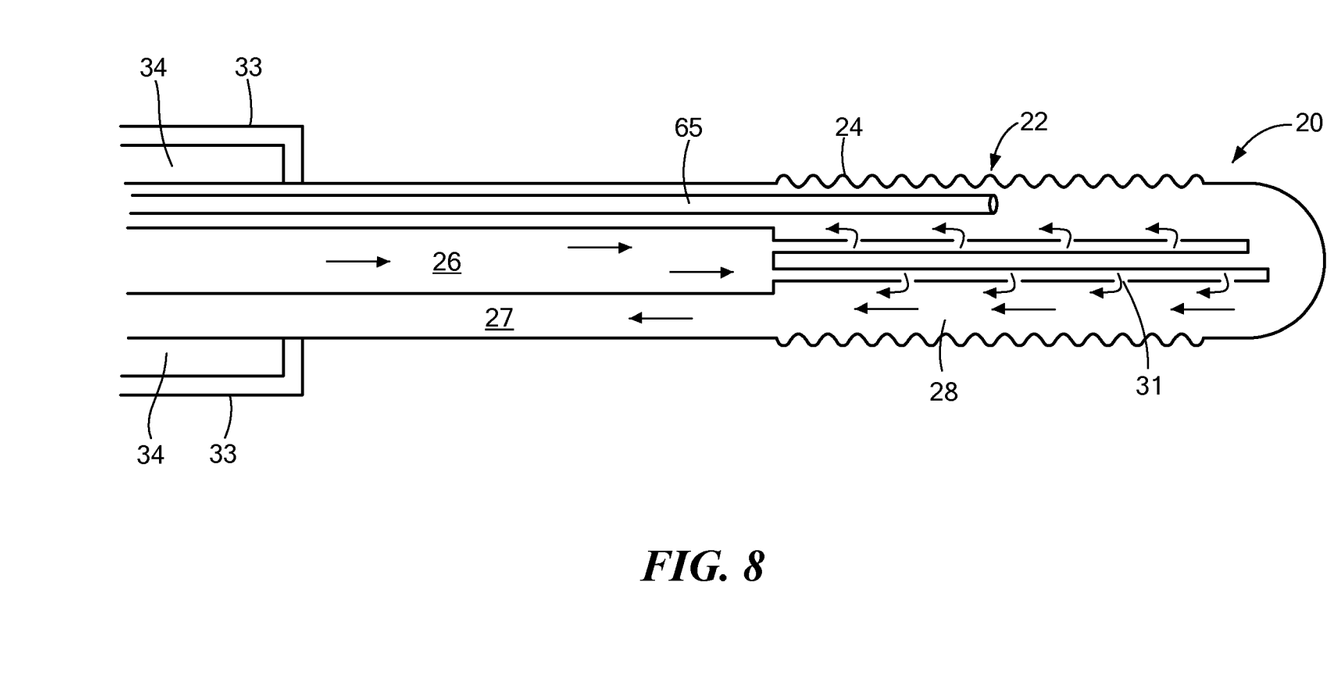
FIG. 8 is a cross-sectional view of an embodiment of an ablation catheter in accordance with the present invention depicting an optical fiber for warming.

Referring to FIGS. 7 and 8, an ablation system in accordance with the present invention is depicted. FIG. 7 is a schematic illustration of a cryosurgical system 10 incorporating means for laser warming of thermally-transmissive region 24. The system includes a supply of cryogenic or cooling fluid 12 in communication with the proximal end of a flexible cryoprobe 20 including operator handle 1. Cryoprobe 20 may alternatively be received within the blades of a cryoclamp 14 as shown in FIG. 3. A regulator 17 is interposed or in-line between the cryogenic fluid supply 12 and a controller 16 or disposed within the controller 16. Controller 16 is in-line between the regulator 17 and the ablation catheter 14 for controlling and regulating the flow of cryogenic fluid into the catheter in response to a controller command. Controller 16 commands can include programmed instructions, sensor signals, and manual user input. For example, the controller 16 can be programmed or configured to increase and decrease the pressure of the fluid by predetermined pressure increments over predetermined time intervals. In another exemplary embodiment, the controller 16 can be responsive to input from a foot pedal to permit flow of the cryogenic fluid into the catheter 20. One or more temperature sensors in electrical communication with the controller 16 can also be provided to regulate or terminate the flow of cryogenic fluid into the catheter 20 when a predetermined temperature at a selected point or points on or within the catheter is/are obtained. A second controller 60 with an integrated laser generation element may be electrically connected to a source of power and may regulate the power of the generated laser. Alternatively, the second controller 60 may be housed within the controller 16 such that regulation of the generated laser power and fluid supply 12 may be achieved from a single controller.

FIG. 8 depicts one or more optical fibers 65 with laser light diffusing tips positioned within the thermally-transmissive region 24. After the cooling/ablation cycle is completed, the optical fiber or fibers scatter(s) light energy inside the thermally-transmissive region and cause(s) the outer probe body to absorb the transmitted light energy causing warming and thawing of the ice ball formed by the cryoprobe during an ablation procedure.

The cryosurgical system in accordance with the invention is further understood with reference to its exemplary use. Following the determination of a proposed lesion site within a heart chamber, for example, the catheter 20 may be directed through a blood vessel to, or positioned surgically on, a region within the heart, such as an atrial or ventricular chamber, where the lesion will be made. The thermally-transmissive region 24 is placed proximate to the tissue to be ablated. The thermally-transmissive region 24 of the catheter may be deformed to conform to the curvature of the tissue before, during, or after placement against the tissue. The controller 16 allows or causes cryogenic fluid to flow from the cryogenic fluid supply 10 to the cooling supply fluid path in the catheter 26 and thence to the thermally-transmissive region 24 to ablate the desired area. The fluid supply line 26 is concentric within a second conduit 27 and cooling fluid travels to the thermally-transmissive region through Joule-Thomson ports 31 and is exhausted from the catheter through second conduit (exhaust fluid path) 27. In an embodiment, warming supply controller 41 is activated and warming fluid circulates through warming fluid supply line 30 and travels to the thermally-transmission region 24 through openings 32 and exhausts into exhaust fluid pathway or chamber 27 thus warming thermally-transmissive region 24. Alternatively, controller 16 may initiate the circulation of warming fluid toward the fluid supply line 30. A second site for ablation may further be chosen and the process of ablating tissue is repeated.

In a second embodiment, the warming fluid is helium. Warming fluid line 11 operably connects to a warming fluid supply container 13. After the cooling/ablating cycle, pressurized helium is circulated into line 26 and expanded through the plurality of Joule-Thomson exhaust ports 31. As helium is Joule-Thomson expanded, the thermally-transmissive region 24 warms and the catheter 20 is released from the tissue. A second site for ablation is chosen and the process of ablating tissue is repeated.

In yet another embodiment, the warming is caused by laser energy. After ablation of the heart tissue at a desired location, the second controller 60 with the integrated laser generation element may be activated. Optical fiber(s) 65 with laser light diffusing tips positioned within the thermally-transmissive region 24 scatter(s) light energy inside the thermally-transmissive region and cause(s) the outer probe body to absorb the transmitted light energy causing warming and thawing of the ice ball formed by the cryoprobe during an ablation procedure. A second site for ablation is chosen and the process of ablating tissue is repeated.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device comprising:
an elongate probe defining a proximal end, a distal end having a distal tip, and a flexible member in the distal end, the flexible member including a thermally-transmissive region, the elongate probe including a first fluid supply line in fluid communication with the thermally-transmissive region, the first fluid supply line being bifurcated at a bifurcation point into a first linear portion and a second linear portion, each of the first and second linear portions extending from the bifurcation point and through the entirety of the thermally-transmissive region; and
an exhaust line in fluid communication with the first and second portions of the first fluid supply line.

2. The medical device of claim 1, further comprising a cryogenic fluid source in fluid communication with the first linear portion of the first fluid supply line and the second linear portion of the first fluid supply line.

3. The medical device of claim 2, further including a controller, wherein the cryogenic fluid source is in fluid communication with the controller.

4. The medical device of claim 2, further comprising a warming fluid source in fluid communication with a second fluid supply line.

5. The medical device of claim 4, wherein the warming fluid source is at least one of argon gas, helium gas, and room temperature air.

6. The medical device of claim 4, further comprising a third fluid supply line in fluid communication with the warming fluid source.

7. The medical device of claim 1, wherein the first linear portion of the fluid supply line is fluidly isolated from the second linear portion of the fluid supply line.

8. The medical device of claim 1, wherein the thermally-transmissive region defines a bellow portion on its outer surface.

9. The medical device of claim 1, wherein the first fluid supply line defines a plurality of ports proximate the distal end.

10. The medical device of claim 1, further including a clamp element having two jaws, and wherein the elongate probe is removably insertable within a portion of one of the jaws.

11. The medical device of claim 1, further comprising a jacket releasably engageable to the elongate probe, the jacket surrounding a portion of the elongate probe.

12. The medical device of claim 1, further including a handle, and wherein the elongate probe is removably insertable within a portion of the handle.

13. The medical device of claim 1, wherein each of the first and second linear portions of the fluid supply line define a plurality of Joule-Thomson orifices.

14. A medical system comprising:
a catheter having a flexible member at its distal end, the flexible member including a thermally-conductive region, the catheter including a fluid injection tube in fluid communication with the thermally-conductive region; the fluid injection tube being bifurcated at a bifurcation point into a first linear portion and a second linear portion, the first linear portion and the second linear portion extending from the bifurcation point and through the entirety of the flexible member;
at least one laser light emitting element disposed within the thermally-conductive region;
a first controller in fluid communication with the fluid injection tube operable to regulate the flow of cryogenic fluid into the thermally-conductive region; and
a second controller in optical communication with the laser light emitting element, the second controller including a laser beam generation element.

15. The medical device of claim 14, wherein the at least one laser light emitting element is an optical fiber defining a plurality of light diffusing tips.

16. The medical device of claim 14, further including a clamp element having two blades, and wherein the catheter is removeably insertable within a portion of one of the blades.

17. The medical device of claim 14, wherein the thermally-conductive region defines a corrugated outer surface.

* * * * *